US008064672B2

(12) United States Patent
Narayanan et al.

(10) Patent No.: US 8,064,672 B2
(45) Date of Patent: Nov. 22, 2011

(54) PATIENT SCAN TIME OPTIMIZATION FOR PET/SPECT IMAGING

(75) Inventors: Manoj Narayanan, Snohomish, WA (US); Bart Jacob Bakker, Eindhoven (NL); Daniel Gagnon, Twinsburg, OH (US); Alexander Fischer, Aachen (DE); Lothar Spies, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 677 days.

(21) Appl. No.: 12/088,088

(22) PCT Filed: Sep. 15, 2006

(86) PCT No.: PCT/IB2006/053317
§ 371 (c)(1),
(2), (4) Date: Jul. 9, 2008

(87) PCT Pub. No.: WO2007/046013
PCT Pub. Date: Apr. 26, 2007

(65) Prior Publication Data
US 2009/0171183 A1  Jul. 2, 2009

Related U.S. Application Data

(60) Provisional application No. 60/727,799, filed on Oct. 18, 2005.

(51) Int. Cl.
*G06K 9/00* (2006.01)
(52) U.S. Cl. ........ 382/131; 382/128; 382/130; 600/407; 600/424; 600/427
(58) Field of Classification Search .................. 600/407, 600/424, 427; 382/128, 130, 131
See application file for complete search history.

(56) References Cited

U.S. PATENT DOCUMENTS

| | | | | |
|---|---|---|---|---|
| 6,343,936 B1 * | 2/2002 | Kaufman et al. | ............. | 434/262 |
| 6,819,796 B2 * | 11/2004 | Hong et al. | .................. | 382/173 |
| 7,136,518 B2 * | 11/2006 | Griffin et al. | ................. | 382/133 |
| 7,282,723 B2 * | 10/2007 | Schomacker et al. | ..... | 250/458.1 |
| 7,309,867 B2 * | 12/2007 | Costa et al. | ................ | 250/458.1 |
| 7,340,375 B1 * | 3/2008 | Patenaud et al. | ............. | 702/180 |
| 7,376,242 B2 * | 5/2008 | Bradley et al. | ................ | 382/100 |
| 7,459,696 B2 * | 12/2008 | Schomacker et al. | ..... | 250/458.1 |
| 7,469,160 B2 * | 12/2008 | Banks et al. | ................... | 600/476 |
| 7,474,776 B2 * | 1/2009 | Kaufman et al. | ............ | 382/128 |
| 7,657,299 B2 * | 2/2010 | Huizenga et al. | ............ | 600/410 |
| 7,769,202 B2 * | 8/2010 | Bradley et al. | ................ | 382/100 |
| 2003/0156684 A1 | 8/2003 | Fessler | | |
| 2005/0226484 A1 * | 10/2005 | Basu et al. | .................... | 382/131 |

OTHER PUBLICATIONS

Chen, Z., et al.; Temporal processing of dynamic positron emission tomography via principal component analysis in the sinogram domain; 2004; IEEE Trans. On Nuclear Science; 51(5)2612-2619.
Watson, C. C., et al.; Evaluation of clinical PET count rate performance; 2003; IEEE Trans. on Nuclear Science; 50 (5)1379-1385.

* cited by examiner

Primary Examiner — Tse Chen
Assistant Examiner — Baisakhi Roy

(57) ABSTRACT

An imaging system (10) comprises a data device (30), which controls radiation data acquisition from a subject positioned in an examination region (18) for an examination. A rebinning processor (40) bins the acquired data periodically into a histogram (42). A transform (70) transforms the histogram (42) into individual independent or uncorrelated components, each component including a signal content and a noise content. A stopping determining device (52) compares an aspect of at least one selected component to a predetermined threshold (TH) and, based on the comparison, terminates the data acquisition.

18 Claims, 2 Drawing Sheets

PATIENT SCAN TIME OPTIMIZATION FOR PET/SPECT IMAGING

CROSS REFERENCE TO RELATED APPLICATIONS

This application claims the benefit of U.S. provisional application Ser. No. 60/727,799 filed Oct. 18, 2005, which is incorporated herein by reference.

The present invention relates to the diagnostic imaging systems and methods. It finds particular application in conjunction with the Positron Emission Tomography (PET) and Single Photon Emission Tomography (SPECT) systems and will be described with particular reference thereto. It will be appreciated that the invention is also applicable to other imaging systems such as Computed Tomography systems (CT), and the like.

Nuclear medicine imaging employs a source of radioactivity to image a patient. Typically, a radiopharmaceutical is injected into the patient. Radiopharmaceutical compounds contain a radioisotope that undergoes gamma-ray decay at a predictable rate and characteristic energy. One or more radiation detectors are placed adjacent to the patient to monitor and record emitted radiation. Sometimes, the detector is rotated or indexed around the patient to monitor the emitted radiation from a plurality of directions. Based on information such as detected position and energy, the radiopharmaceutical distribution in the body is determined and an image of the distribution is reconstructed to study the circulatory system, radiopharmaceutical uptake in selected organs or tissue, and the like.

Typically, the acquisition of PET images takes from only few minutes to about thirty minutes and sometimes even longer. These longer duration scans are an unpleasant experience for many patients, as the patients are required to lie still throughout the duration of the scan. It is highly desirable to reduce the scan time to increase patient comfort and throughput of the clinics while maintaining adequate image quality.

One approach to reduce the scan acquisition time is to improve the sensitivity of the scanner. However, a substantial improvement in the scanner sensitivity is costly. Another approach to reduce the acquisition time is to define the stopping point or stopping criteria of data acquisition. The PET and SPECT acquisitions are count-based. Presently, the scan time per bed position is determined in advance to ensure a good image quality based on a predicted number of counts. Some methods used to determine the adequate scanning time or the desired number of counts include factors such as the clinician's experience, manufacturer's recommendations, recommendations cited in the literature, and others. Other methods include patient weight, injected dose, and the type of study. However, the desired number of counts is determined before the study starts and is not modified or optimized as the scan progresses. Some automated methods for optimizing scans times for the PET imaging include the Noise Equivalent Count (NEC) criteria which represents the effectiveness of the count, and using count density within a region of interest (ROI) for statistical reconstruction methods. However, because these automated methods are based on historical characteristics of similar studies, these methods do not optimally define a stopping criteria on a patient-by-patient basis.

The present invention provides new and improved apparatuses and methods, which overcome the above-referenced problems and others.

In accordance with one aspect, an imaging system is disclosed. A data device controls radiation data acquisition from a subject positioned in an examination region for an examination. A rebinning processor bins the acquired data periodically into a histogram. A transform transforms the histogram into individual independent or uncorrelated components, each component including a signal content and a noise content. A stopping determining device compares an aspect of at least one selected component to a predetermined threshold and, based on the comparison, terminates the data acquisition.

In accordance with another aspect, an imaging method is disclosed. Radiation data acquisition from a subject positioned in an examination region for an examination is controlled. The acquired data is binned into a histogram. The histogram is periodically transformed into individual independent or uncorrelated components, each component including a signal content and a noise content. An aspect of at least one selected component is compared to a preselected termination criteria. Based on the comparison, the data acquisition is terminated or continued.

In accordance with yet another aspect, an imaging system is disclosed. A data device controls data acquisition, and splits the acquired data into data sets of a predefined duration. A rebinning processor bins the acquired data into a histogram. A processor is programmed to perform steps of: transforming the histogram of each data set into individual independent components, each component including a signal content and a noise content, selecting individual components for processing based on a predetermined criteria, determining a variance of each selected component, which variance is representative at least of one of the signal and noise content, comparing the determined variance of each selected component to a threshold, and based on the comparison, one of terminating and continuing the data acquisition.

One advantage resides in dynamically adjusting the stopping criteria during a scan.

Another advantage resides in minimizing scan times.

Another advantage resides in reducing retakes due to a first scan resulting in statistically unreliable image.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
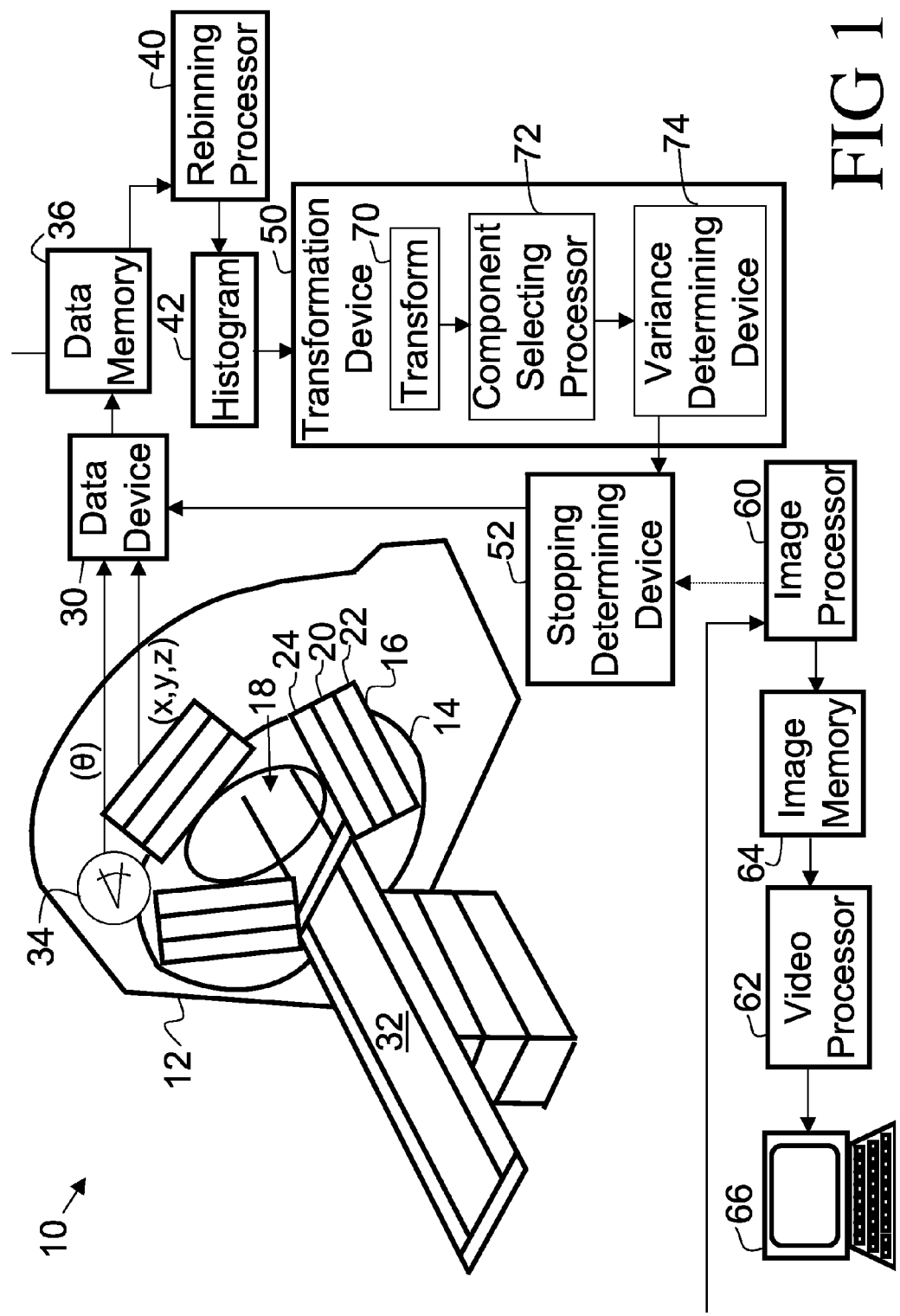
FIG. 1 is a diagrammatic illustration of an imaging system.

With reference to FIG. 1, a nuclear imaging system 10 typically includes a stationary gantry 12 that supports a rotatable gantry 14. One or more detection heads 16 are carried by the rotatable gantry 14 to detect radiation events emanating from a region of interest or examination region 18. Alternatively, particularly in a PET scanner, the examination region is typically surrounded by a ring of stationary detector heads. Each detection head includes two-dimensional arrays of detector elements or detector 20 such as a scintillator and light sensitive elements, e.g. photomultiplier tubes, photodiodes, and the like. Direct x-ray to electrical converters, such as CZT elements, are also contemplated. Each head 16 includes circuitry 22 for converting each radiation response into a digital signal indicative of its location (x, y) on the detector face and its energy (z). The location of an event on the detector 20 is resolved and/or determined in a two dimensional (2D) Cartesian coordinate system with nominally termed x and y coordinates. However, other coordinate systems are contemplated. Particularly, in a SPECT scanner, a scatter grid and/or collimator 24 controls the direction and angular spread, from which each element of the detector 20 can receive radiation. The collimator limits the reception of radiation only along known rays. Thus, the determined location on the detector 20 at which radiation is detected and the angular position of the camera 16 define the nominal ray along which each radiation event occurred.

A data device or controller or means 30 controls the data acquisition. More specifically, typically, an object to be imaged is injected with one or more radiopharmaceuticals or radioisotopes and placed in the examination region 18 supported by a couch 32. Few examples of such isotopes are F-18, C-11, Tc-99m, Ga-67, and In-111. The presence of the radiopharmaceuticals within the object produces emission radiation from the object. Radiation is detected by the detection heads 16 around the examination region 18 to collect the projection emission or coincidence data.

In one embodiment, the data device 30 acquires the projection data in a set of n sequential in time PET sinograms of a short duration, for example, 10 seconds each. The data might be acquired in list-mode or frame-mode format. The projection emission data, e.g. the location (x, y), energy (z), and an angular position (θ) of each detection head 16 around the examination region 18 (e.g., obtained from an angular position resolver 34) are stored in a data memory 36. As the data is being acquired, a rebinning processor or device or means 40 bins the acquired data into a histogram 42 which represents a number of counts versus ray through the patient, e.g. the number of counts along each ray. With very noisy data, the number of events along each ray will begin and stay relatively equal. With lower noise data, the events will cluster in progressively more concentrated clusters along a subset of rays, particularly, the rays which intersect concentrations of the radioisotope. That is, the ray of the subset will have very high numbers of events relative to other rays. As discussed in detail below, a transformation processor or algorithm or means 50 performs a data analysis on the histogram 42 accumulated since the beginning of the data acquisition. More specifically, the acquired data is transformed into variables or components by using sub-space transforms that have identified properties.

The transforms are selected, for example, to enable simpler analysis of multivariate data using the properties of derived variables such as data redunduncies (correlations), separability, orthogonality, and dimensionality reduction. Often, the original representation of the data can contain redundancies due to correlations between many of the variables. By appropriately transforming the measured data into derived variables, a more compact representation of the data is achieved by neglecting those variables whose variations are smaller than that of measurement noise.

A stopping determining device 52 determines a scan stopping point or criteria by optimizing the signal-to-noise tradeoff. An image processor 60 reconstructs data into volumetric image representation. A video processor 62 receives slices, projections, 3D renderings, and other image information from an image memory 64 and appropriately formats an image representation for display on one or more human viewable displays, such as a video monitor 66, printer, storage media, or the like.

With continuing reference to FIG. 1, a transform 70 computes the Karhunen-Loeve (KL) basis function (from the histogram 42. The KL transform is commonly used for performance evaluation of compression algorithms in digital signal processing since it has been proven to be an optimum transform for the compression of a sampled sequence in the sense that the KL spectrum contains the largest number of zero-valued coefficients. Because the basis functions of the KL transform are data dependent, the KL spectrum is generally used as a benchmark to judge the effectiveness of the data compression capability of other more easily computed transforms such as, for example, Fourier transform.

The KL transform is also commonly used in clustering analysis to determine a new coordinate system for sample data where the largest variance of a projection of the data lies on the first axis, the next largest variance on the second axis, and so on. Because the axes are orthogonal, this approach allows for reducing the dimensionality of the data set by eliminating those coordinate axes with small variances. Such a data reduction technique is commonly referred to as the Principal Component Analysis. Upon transformation, most of the signal content is stored in the first few components with the higher order components being dominated by noise. The KL basis vectors are the orthogonal eigenvectors of the temporal covariance function matrix of the input data.

Since the number of the time frames acquired by the data device 30 is usually small, the basis function Φ can be quickly estimated. A component selecting processor or algorithm or means 72 eliminates those components of the basis function Φ which have small variances such as a first component and those components of the basis function Φ, which have larger variances such as higher order components dominated by noise, for data analysis. In one embodiment, the component selecting means 72 selects second, third and fourth components for data analysis. For example, a first KL-component represents a maximum amount of signal variation and thus varies relatively slowly. Therefore, it is more practical to evaluate the variance associated with other components that are dominated by noise more than the first component because such noise dominated components exhibit more variance. From the other side, the higher order components are largely dominated by noise and include very little signal content.

A variance determining device or means or algorithm 74 determines variance associated with each selected KL-component. The relative variance Var in each component may be described as $$Var_i = \lambda_i \bigg/ \sum_{i=1}^{n} \lambda_i,$$

where $\lambda_i$ represents the eigenvalue corresponding to the $i^{th}$ KL-component.

Using the signal content as a criteria, an optimal stopping criteria for the imaging scans can be determined. More specifically, the stopping determining device 52 compares the determined variance Var to a pre-defined threshold $T_H$, such as from about 25% to about 1%, and determines the scan stopping point. If the determined variance Var is less than the pre-defined threshold $T_H$, the scan stopping point is reached. E.g., the count statistics are sufficient for adequate image quality. If the determined variance Var is greater than or equal to the pre-defined threshold $T_H$, the scan stopping point is not reached yet. E.g., the count statistics are not sufficient for adequate image quality. The data device 30 acquires an additional time frame. The rebinning processor 40 bins the acquired data into the histogram 42. The transform 70 computes the Karhunen-Loeve basis function (from the histogram 42. The component selecting processor 72 selects components for data analysis. The variance determining device 74 determines variance Var associated with each selected KL-component. The stopping determining device 52 compares the determined variance Var to the pre-defined threshold $T_H$ to determine whether the scan stopping point is reached. The process is repeated until the threshold criteria of minimum variance is met. In this manner, through predefined data transformations, an automated technique computes in real time an optimal scan stopping point by effective discrimination between the signal and noise content.

In one embodiment, the data device 30 acquires the radiation data based on the determined variance. More specifically, for the lower variance, the data is acquired in more frequent time intervals. For the greater variance, the data is acquired in larger time intervals. Accordingly, for example, for the lower variance, the stopping determining device 52 determines the stopping criteria more frequently to stop the data acquisition sooner.

In one embodiment, where the patient information is available, the method described above is restricted to the region of interest of the patient. E.g., the variance determining 74 determines variance only in the region of interest.

Figure 2:
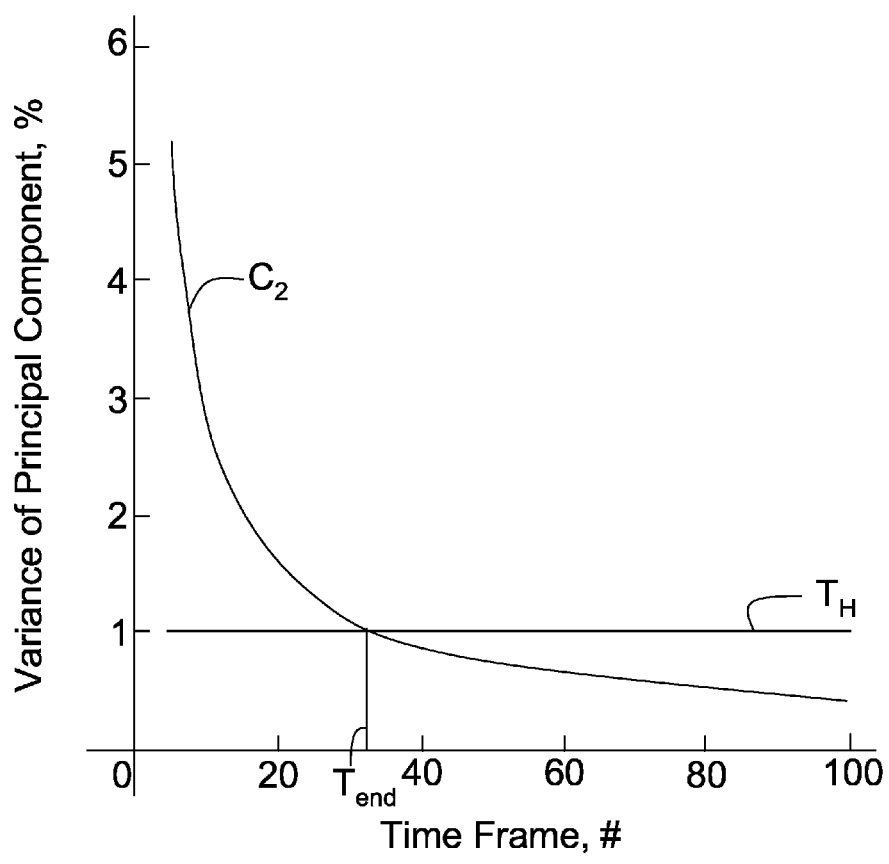
FIG. 2 is a graph demonstrating dependence of a variance in one of the components versus acquired data frames.

With reference to FIG. 2, as the number of additional scans is augmented, the variance Var associated with a second component $C_2$ decreases, correspondingly to a point $T_{END}$ where no significant additional benefit is gained by prolonging the duration of the scan. Such well defined data collection termination point $T_{END}$ ensures quicker imaging scans which are fully exposed or defined and provides the potential for greater patient throughput in the clinics and better accommodations for the patients during the duration of the scan. Of course, other or additional termination criteria are also contemplated. For example, termination can be in response to the variance ceasing to improve or starting to degrade. The methodology described above adapts easily within the clinical workflow, resulting in reduced scan times on a patient-by-patient basis, while maintaining optimal image quality of the acquired data.

Of course, it is also contemplated, that other types of data analysis, such as independent component analysis, singular value decomposition, Fourier transform, and the like are used. The transforms which might be selected depend on the characteristics of the data to be analyzed. The threshold may vary with the type of examination, the region of the patient, the weight of the patient, and other such factors. In one embodiment, the threshold is determined by considering several images obtained by prior scans which are thought to be good images by clinicians. The above analysis is performed on the data from which the image was generated, the variance is determined, and the threshold is set based on the determined variance.

In one embodiment, a similar analysis and the data collection termination method as described above is used on the reconstructed image or on data during the reconstruction process. The analysis is adjusted to accommodate changes in noise characteristics during the reconstruction processing.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. An imaging system including:
   a data device, which controls radiation data acquisition from a subject positioned in an examination region for an examination;
   a rebinning processor which, as the data is continuing to be acquired, periodically bins accumulated radiation data into a histogram;
   a transform processor, which transforms the histogram into individual independent or uncorrelated components, each component including a signal content and a noise content;
   a variance determining device which determines a variance of at least one selected component; and
   a stopping determining device, which compares an aspect of the at least one selected component to a predetermined threshold and, based on the comparison, terminates the data acquisition.

2. The system as set forth in claim 1, wherein the aspect of each selected component includes the variance of an associated selected component, which variance is representative of the noise content of the selected component.

3. The system as set forth in claim 1, wherein the data acquisition is terminated if the determined variance is less than about 5% and the data acquisition continues if the determined variance is greater than about 5%.

4. The system as set forth in claim 1, further including:
   a component selecting processor, which selects components for processing by the variance determining device based on a predetermined criteria.

5. The system as set forth in claim 4, wherein the criteria is indicative of a signal to noise ratio.

6. The system as set forth in claim 1, wherein the periodicity of binning the accumulated radiation data into the histogram is based at least on one of:
   predetermined time intervals, and
   the determined variance.

7. The system as set forth in claim 1, wherein the transform executes at least one of:
   Principal Component Analysis,
   Independent Component Analysis,
   Singular Value Decomposition, and
   Fourier transform.

8. The system as set forth in claim 7, wherein the transform executes Karhulen-Loeve transform.

9. The system as set forth in claim 1, further including:
   at least one of a PET scanner and a SPECT scanner, which includes at least one radiation detection head disposed adjacent the examination region to detect emission radiation from the subject and generate the radiation data.

10. A nuclear imaging method comprising:
    acquiring emission radiation data;
    during the radiation data acquisition, binning accumulated radiation data into a histogram;
    periodically transforming the histogram into individual independent or uncorrelated components, each component including a signal content and a noise content;
    comparing an aspect of at least one selected component to a preselected termination criteria, the aspect of the selected component including a variance of an associated selected component, which variance is representative of the noise content of the selected component; and
    based on the comparison, terminating or continuing data acquisition.

11. The method as set forth in claim 10, further including:
    terminating the data acquisition if the variance is less than about 5%; and
    continuing the data acquisition if the variance is greater than or equal to about 5%.

12. The method as set forth in claim 10, wherein the radiation data is acquired in preselected sequential time intervals, the method further including:
   binning the accumulated radiation data from the preceding time interval into the histogram; and
   transforming the histogram into individual independent or uncorrelated components.

13. The method as set forth in claim 10, wherein the step of transforming executes at least one of:
   Principle Component Analysis,
   Independent Component Analysis,
   Singular Value Decomposition, and
   Fourier transform.

14. The method as set forth in claim 13, wherein the step of transforming executed Karhulen-Loeve transform.

15. An imaging system comprising of one of more processors programmed to perform the method of claim 10.

16. An imaging system comprising:
   a data device, which controls radiation data acquisition from a subject positioned in an examination region for an examination;
   at least one processor programmed to perform the steps of:
      during the radiation data acquisition, binning accumulated radiation data into a histogram,
      periodically transforming the histogram into components, each component including a signal content and a noise content;
      determining a variance of one or more of the components;
      comparing the variance to a preselected termination criteria; and
      based on the comparison, terminating or continuing the data acquisition.

17. The method as set forth in claim 16, wherein determining the variance includes:
   determining the variance in a region of interest of the subject.

18. An imaging system, comprising:
   a data device which controls data acquisition, and splits the acquired data into data sets of a predefined duration;
   a rebinning processor which bins the acquired data into a histogram; and
   a processor which is programmed to perform steps of:
      transforming the histogram of each data set into individual independent components, each component including a signal content and a noise content,
      selecting individual components for processing based on a predetermined criteria,
      determining a variance of each selected component which variance is representative at least of one of the signal and noise content,
      comparing the determined variance of each selected component to a threshold, and
      based on the comparison, one of terminating and continuing the data acquisition.

* * * * *